United States Patent
Paul et al.

(10) Patent No.: US 7,271,910 B2
(45) Date of Patent: Sep. 18, 2007

(54) SYSTEMS AND METHODS FOR COMPENSATING FOR TEMPERATURE INDUCED SPECTRAL EMISSION VARIATIONS IN LED BASED COLOR PARAMETER MEASURING DEVICES

(75) Inventors: Peter Paul, Webster, NY (US); Lalit K. Mestha, Fairport, NY (US); Claude S. Fillion, Rochester, NY (US); R. Enrique Viturro, Rochester, NY (US)

(73) Assignee: Xerox Corporation, Stamford, CT (US)

( * ) Notice: Subject to any disclaimer, the term of this patent is extended or adjusted under 35 U.S.C. 154(b) by 275 days.

(21) Appl. No.: 11/092,674

(22) Filed: Mar. 30, 2005

(65) Prior Publication Data

US 2006/0221341 A1    Oct. 5, 2006

(51) Int. Cl.
    *G01N 21/25* (2006.01)
(52) U.S. Cl. ...................................... 356/406; 356/408
(58) Field of Classification Search ................. 356/406, 356/408
    See application file for complete search history.

(56) References Cited

U.S. PATENT DOCUMENTS

| | | | |
|---|---|---|---|
| 4,917,500 A * | 4/1990 | Lugos | 356/406 |
| 5,257,097 A * | 10/1993 | Pineau et al. | 358/500 |
| 6,449,045 B1 | 9/2002 | Mestha | |
| 6,556,300 B2 | 4/2003 | Tandon et al. | |
| 6,556,932 B1 | 4/2003 | Mestha et al. | |
| 6,567,170 B2 | 5/2003 | Tandon et al. | |
| 6,584,435 B2 * | 6/2003 | Mestha et al. | 702/196 |
| 6,587,793 B2 | 7/2003 | Viassolo et al. | |
| 6,603,551 B2 | 8/2003 | Mestha et al. | |
| 6,621,576 B2 | 9/2003 | Tandon et al. | |
| 6,633,382 B2 | 10/2003 | Hubble, III et al. | |
| 6,721,692 B2 * | 4/2004 | Mestha et al. | 702/196 |
| 2003/0050768 A1 * | 3/2003 | Mestha et al. | 702/196 |
| 2003/0055575 A1 * | 3/2003 | Viassolo et al. | 702/27 |
| 2003/0055611 A1 * | 3/2003 | Mestha et al. | 702/196 |

OTHER PUBLICATIONS

U.S. Appl. No. 10/758,096, filed Jan. 16, 2004, Mestha et al.

* cited by examiner

*Primary Examiner*—Roy M. Punnoose
(74) *Attorney, Agent, or Firm*—Oliff & Berridge, PLC

(57) ABSTRACT

Systems and method provide compensation for temperature induced peak wavelength shift of LEDs is color parameter measuring systems that use a model to reconstruct target color parameter values from the reflectance values measured when the target is illuminated by LEDs. Several models may be constructed, with each model being trained at a unique temperature, resulting in a set of models that span the temperature range of interest. In real-time, the LED based color parameter measuring system measures the temperature and interpolates between the models to estimate the appropriate model to use at the temperature of interest. The estimated model is then used to perform the color parameter value estimation.

34 Claims, 5 Drawing Sheets

US 7,271,910 B2

SYSTEMS AND METHODS FOR COMPENSATING FOR TEMPERATURE INDUCED SPECTRAL EMISSION VARIATIONS IN LED BASED COLOR PARAMETER MEASURING DEVICES

INCORPORATION BY REFERENCE

Cross-reference and incorporation by reference are made to the following co-pending and commonly assigned U.S. patent applications and/or the following U.S. patents: U.S. Pat. No. 6,584,435, U.S. Pat. No. 6,587,793, U.S. Pat. No. 6,556,932, U.S. Pat. No. 6,449,045, U.S. Pat. No. 6,556,300, U.S. Pat. No. 6,567,170, U.S. Pat. No. 6,633,382, U.S. Pat. No. 6,621,576, U.S. Pat. No. 6,603,551, U.S. Pat. No. 6,721,692, and co-pending, commonly assigned U.S. patent application Ser. No. 10/758,096.

BACKGROUND

Automatic in-line color calibration systems can be much more effective with an in-line color measurement system where a spectrophotometer may be mounted in the paper path of the moving copy sheets in the printer, preferably in the output path after fusing or drying, without having to otherwise modify the printer, or interfere with or interrupt normal printing, or the movement of the printed sheets in said paper path, and yet provide accurate color measurements of test color patches printed on the moving sheets as they pass the spectrophotometer. That enables a complete closed loop color control of a printer.

A typical spectrophotometer gives color information in terms of measured reflectances or transmittances of light, at the different wavelengths of light, from the test surface. This spectrophotometer desirably provides distinct electric signals corresponding to the different levels of reflected light received from the respective different illumination wavelength ranges or channels.

Known devices capable of providing distinct electric signals corresponding to the different levels of reflected light received from the respective different illumination wavelength ranges or channels include a grating-based spectrophotometer made by Ocean Optics Inc., LED based sensors marketed by "ColorSavvy" or Accuracy Microsensor; and other spectrophotometers by Gretag MacBeth (Viptronic), ExColor, and X-Rite (DTP41). However, those devices are believed to have significant cost, measurement time, target displacement errors, and/or other difficulties, for use in real-time printer in-line measurements.

As used herein, unless otherwise specifically indicated, the term "spectrophotometer" may encompass a spectrophotometer, colorimeter, and densitometer, as broadly defined herein. The definition or use of such above terms may vary or differ among various scientists and engineers. However, the following is an attempt to provide some simplified clarifications relating and distinguishing the respective terms "spectrophotometer," "colorimeter," and "densitometer," as they may be used in the specific context of specification examples of providing components for an in-line color printer color correction system, but not necessarily as claim limitations.

A typical "spectrophotometer" measures the reflectance of an illuminated object of interest over many light wavelengths. Typical prior spectrophotometers in this context use 16 or 32 channels measuring from 380 nm to 730 nm or so, to cover the humanly visible color spectra or wavelength range. A typical spectrophotometer gives color information in terms of measured reflectances or transmittances of light, at the different wavelengths of light, from the test surface. (This is to measure more closely to what the human eye would see as a combined image of a broad white light spectra image reflectance, but the spectrophotometer desirably provides distinct electrical signals corresponding to the different levels of reflected light from the respective different illumination wavelength ranges or channels.)

A "colorimeter" normally has three illumination channels, red, green and blue. That is, generally, a "colorimeter" provides its three (red, green and blue or "RGB") values as read by a light sensor or detector receiving reflected light from a color test surface sequentially illuminated with red, green and blue illuminators, such as three different color LEDs or one white light lamp with three different color filters. It may thus be considered different from, or a limited special case of, a "spectrophotometer," in that it provides output color information in the trichromatic quantity known as RGB.

Trichromatic quantities may be used for representing color in three coordinate space through some type of transformation. Other RGB conversions to "device independent color space" (i.e., RGB converted to conventional $L^*a^*b^*$) typically use a color conversion transformation equation or a "lookup table" system in a known manner.

A "densitometer" typically has only a single channel, and simply measures the amplitude of light reflectivity from the test surface, such as a developed toner test patch on a photoreceptor, at a selected angle over a range of wavelengths, which may be wide or narrow. A single illumination source, such as an IR LED, a visible LED, or an incandescent lamp, may be used. The output of the densitometer detector is programmed to give the optical density of the sample. A densitometer of this type is basically "color blind." For example, a cyan test patch and magenta test patch could have the same optical densities as seen by the densitometer, but, of course, exhibit different colors.

SUMMARY

A multiple LED reflectance spectrophotometer, as in the examples of the embodiments herein, may be considered to belong to a special class of spectrophotometers which normally illuminate the target with multiple instances of narrow band. Others, with wide band illumination sources, can be flashed Xenon lamp spectrophotometers, or incandescent lamp spectrophotometers. A spectrophotometer is normally programmed to give more detailed reflectance values by using more than 3 channel measurements (for example, 10 or more channel measurements), with conversion algorithms. That is in contrast to normal three channel colorimeters, which cannot give accurate, human eye related, reflectance spectra measurements, because they have insufficient measurements for that (only 3 measurements).

It is desirable for a printer color control system to dynamically measure the color of test patches on the printed output media "in line," that is, while the media is still in the sheet transport or paper path of a print engine, for real-time and fully automatic printer color correction applications.

For a low cost implementation of the color sensor, a multiple illuminant device is used as the illumination source, and has, for example, 8, 10, 12 or 16 LEDs. Each LED is selected to have a narrow band response curve in the spectral space. Therefore, for example, ten LEDs would correspond to ten measurements in the reflectance curve. The LEDs, or other multiple illuminant based color sensor equivalent, e.g., lasers, are switched on one at a time as, for example, the measured media is passed through a transport of a printer. The reflected light is then detected by a photodetector and the corresponding voltage integrated and normalized with a white tile.

To obtain a smooth curve similar to that of a Gretag spectrophotometer, linear or cubic spline algorithms could be used, which blindly interpolate the data points without knowledge of the color space. Unfortunately, due to lack of measurements at wavelengths below 430 nm and above 660 nm (due to lack of LEDs at these wavelengths), extrapolation with 10 measurements can lead to errors.

U.S. Pat. No. 6,584,435, U.S. Pat. No. 6,587,793, U.S. Pat. No. 6,556,932, and U.S. Pat. No. 6,449,045 collectively disclose various systems and methods for using the integrated sensor measurements to determine a fully populated reflectance spectra with reflectance values at specific wavelengths. Those methods and systems use a reference database in determining the spectra, and convert integrated multiple illuminant measurements from a non-fully illuminant populated color sensor into a fully populated spectral curve. As described collectively in these disclosures, the reference database is generated by measuring the reflectance spectra of some set of reference colors, with an accurate reference spectrophotomer, such as a Gretag spectrophotometer, and their corresponding LED sensor outputs, with the sensor array of a given color measuring device. In general, the more densely populated the database is, i.e., the more reference colors used, the better the resulting accuracy. Furthermore, even spacing of the reference colors in the color space gives greater accuracy. The data stored in the reference database will be referred to hereafter as the training samples.

Co-pending U.S. patent application Ser. No. 10/758,096 relates to a reference database usable with the above-described systems, and a method for constructing the reference database, and a method of using the reference database to obtain a spectral curve. In embodiments, the database is partitioned into a plurality of clusters, and an appropriate centroid is determined for each cluster. In embodiments, the centroids are obtained by vector quantization. The training samples may be assigned to the clusters by comparing the Euclidean distance between the centroids and the sample under consideration, and assigning each sample to the cluster having the centroid with the shortest Euclidean distance. When all training samples have been assigned, the resulting structure is stored as the reference database.

In co-pending U.S. patent application Ser. No. 10/758, 096, when reconstructing the spectra for new measurements from the sensor, the Euclidean distances between actual color samples under measurement and each cluster centroid are calculated. The spectra are then reconstructed using only the training samples from the cluster corresponding to the shortest Euclidean distance. By thus using only a limited number of the total training samples, the speed and accuracy of the spectral reconstruction is enhanced.

Spectrophotometers that use multiple LEDs of various peak wavelengths to determine target spectral reflectivity require stable and accurate measurements under all operating conditions through the use of solid-state illumination sources, such as LEDs. However, the LED based illumination sources may not be stable under operating temperature changes. The total light output power of the LEDs as well as the peak wavelength of the emission spectra of the LEDs may change with temperature.

Temperature induced variations in total light output power of the LEDs may be compensated using a feed-forward model based technique using a temperature sensor or using a calibration technique to a reference target, and adjusting either LED drive current or LED duty cycle for a system that integrates received light power with time. The received signal may also be amplified or digitally scaled to compensate for total light output power variations with temperature. Typically, temperature induced variations in LED emission spectra, dominantly manifested in shifts in peak wavelength and in changes in the full-width half maximum of the emission, are ignored. However, when temperature induced variations are ignored, either operating temperature range of the device is compromised, or accurate performance of the spectrophotometer and resulting color measurements is compromised. Therefore, embodiments according to this disclosure account for temperature variations.

When embedded in a marking engine for feedback control of output color of a printing system, the spectrophotometer may be subject to a wide range of temperatures, depending on its placement in the system and the subsystems that comprise the printing system. Thus, temperature compensation may be needed for the spectrophotometer to accurately and stably measure target spectral reflectivity under varying operating temperature conditions.

Systems and methods disclosed herein provide compensation for temperature induced peak wavelength shift of LEDs in spectrophotometers that use a model to reconstruct target reflectance spectra from the reflectance values measured when the target is illuminated by LEDs. Several models may be constructed, with each model being trained at a unique temperature, resulting in a set of models that span the temperature range of interest. In real-time, the LED based spectrophotometer measures the temperature and interpolates between the models, if necessary, to estimate the appropriate model to use at the temperature of interest. The estimated model is then used to perform the spectral reconstruction.

Compensation may be provided for temperature-induced peak wavelength shift of LEDs in spectrophotometers that use a model to reconstruct target reflectance spectra from the reflectance values measured when the target is illuminated by LEDs. Several models may be constructed, with each model being trained at a unique temperature, resulting in a set of models that span the temperature range of interest. In real-time, the LED based spectrophotometer measures the temperature and interpolates between the models to estimate the appropriate model for a cluster containing a plurality of colors to use at the temperature of interest. The estimated model is then used to perform the spectral reconstruction.

These and other features and details are described in, or are apparent from, the following detailed description.

BRIEF DESCRIPTION OF THE DRAWINGS

Various exemplary details of systems and methods are described with reference to the following figures, wherein like numerals represent like parts, and wherein.

DETAILED DESCRIPTION

Figure 1:
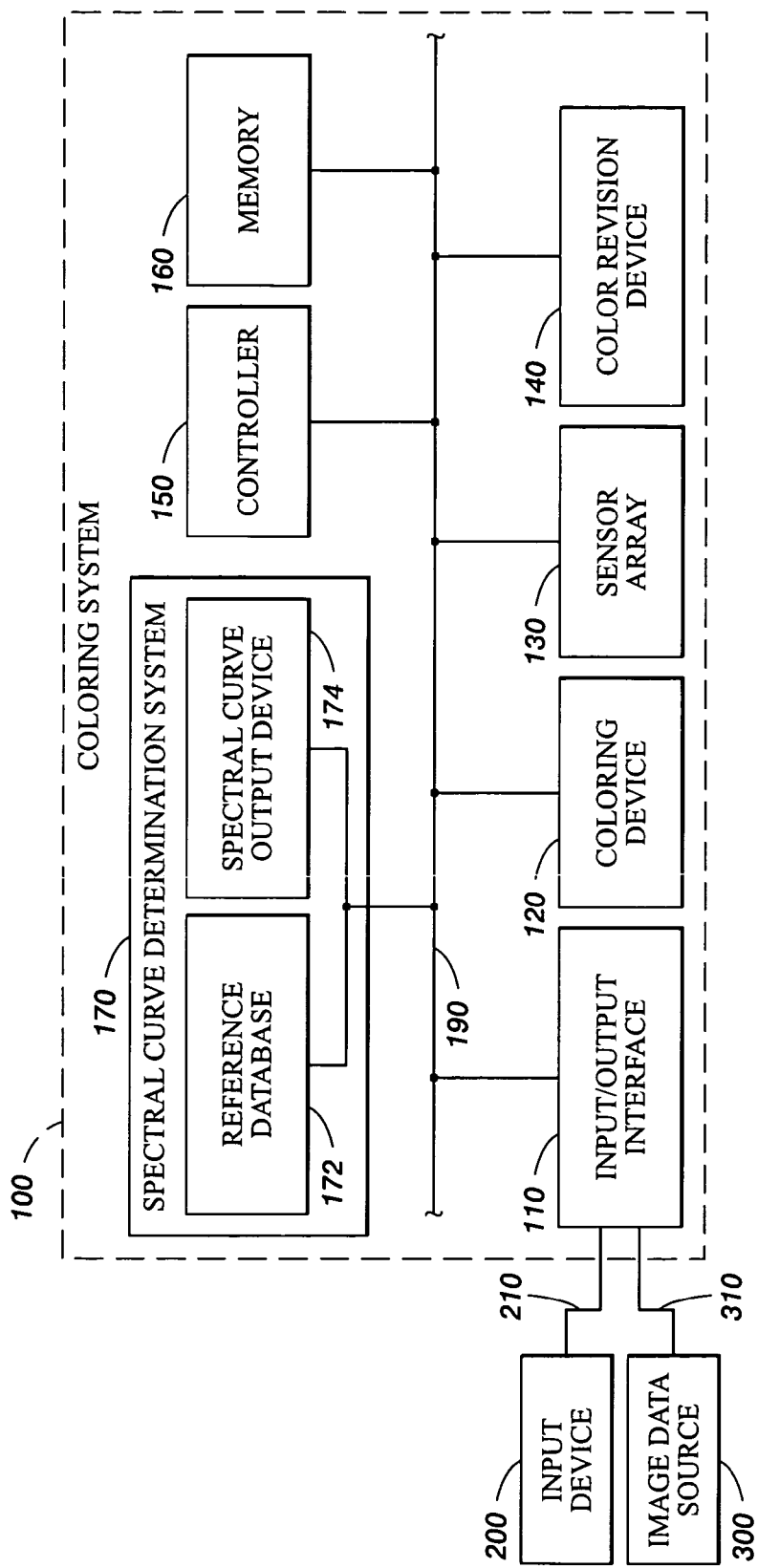
FIG. 1 is a functional block diagram illustrating an exemplary embodiment of a coloring system.

A spectrophotometer may be mounted at the printed side of a sheet output path of a color printer to optically evaluate color imprinted output sheets as they move past the spectrophotometer, variably spaced therefrom, without having to contact the sheets or interfere with the normal movement of the sheets. In particular, it may be used to measure a number of color test patch samples printed by the printer on actual printed sheet output of the printer during regular or selected printer operation intervals (between normal printing runs or print jobs). These color test sheet printing intervals may be at regular timed intervals, and/or at each machine "cycle-up," or as otherwise directed by the system software. The spectrophotometer may be mounted at one side of the paper path of the machine, or, if it is desired to use duplex color test sheets, two spectrophotometers may be mounted on opposite sides of the paper path.

Relatively frequent color calibration of a color printer is highly desirable, since the colors actually printed on the output media (as compared to the colors intended to be printed) can significantly change, or drift out of calibration over time, for various known reasons. For example, changes in the selected or loaded print media, such as differences in paper or plastic sheet types, materials, weights, calendaring, coating, humidity, etc., or changes in the printer's operating conditions, changes in the image developer materials, aging or wear of printer components, varying interactions of different colors being printed, etc. Printing test color patches on test sheets of the same print media under the same printing conditions during the same relative time periods as the color print job being color-controlled is thus very desirable.

It is thus also advantageous to provide dual-mode color test sheets, in which multiple color patches of different colors are printed on otherwise blank areas of each, or selected, banner, cover, or other inter-document or print job separator sheets. Different sets of colors may be printed on different banner or other test sheets. This dual use of such sheets saves both print paper and printer utilization time, and also provides frequent color calibration opportunities where the printing system is one in which banner sheets are being printed at frequent intervals anyway.

An additional feature which can be provided is to tailor or set the particular colors or combinations of the test patches on a particular banner or other test sheet to those colors which are about to be printed on the specific document for that banner sheet, i.e., the document pages which are to be printed immediately subsequent to that banner sheet (the print job identified by that banner sheet). This can provide a "real time" color correction for the color printer which is tailored to correct printing of the colors of the very next document to be printed.

It will be appreciated that these test patch images and colors may be automatically sent to the printer imager from a stored data file specifically designed for printing the dual mode banner sheet or other color test sheet page, and/or they may be embedded inside the customer job containing the banner page. That is, the latter may be directly electronically associated with the electronic document to be printed, and/or generated or transmitted by the document author or sender. Because the printed test sheet color patches colors and their printing sequence is known (and stored) information, the in-line spectrophotometer measurement data therefrom can be automatically coordinated and compared.

After the spectrophotometer or other color sensor reads the colors of the test patches, the measured color signals may be automatically processed inside the system controller or the printer controller to produce or modify the tone reproduction curve, as explained in the cited references. The color test patches on the next test sheet may then be printed with that new tone reproduction curve. This process may be repeated so as to generate further corrected tone reproduction curves. If the printer's color image printing components and materials are relatively stable, with only relatively slow long term drift, and there is not a print media or other abrupt change, the tone reproduction curve produced using this closed loop control system will be the correct curve for achieving consistent colors for at least one or even a substantial number of customer print jobs printed thereafter, and only relatively infrequent and few color test sheets, such as the normal banner sheets, need be printed. Note that the printer multidimensional color calibration tables may also be modified to perform the compensation, in addition to the single dimensional tone reproduction curves.

In addition to use in printers, it should be noted that color measurements, and/or the use of color measurements for various quality or consistency control functions, are also important for many other different technologies and applications, such as in the production of textiles, wallpaper, plastics, paint, inks, food products, etc. and in the measurement or detection of various properties of various materials, objects or substances. Thus, the systems and methods disclosed herein may have applications in various such other fields where these materials, objects or substances are to be color tested, including both (1) applications in which color measurements are taken and applied in a closed loop control system and (2) applications in which the measurement result is not fed back into a control loop, but is used to generate a one-time output.

FIG. 1 is a functional block diagram illustrating an exemplary embodiment of a coloring system 100. The coloring system 100 is connected to an input device 200 via a link 210. The input device 200 inputs various information needed to implement the operations of the coloring system 100, as described in more detail below, and may include a mouse, a keyboard, a touch-screen input device, a voice recognition-based input device, and/or any other known or later developed device usable for inputting information. The coloring system 100 optionally is connected to an image data source 300 via a link 310. The connection to the image data source 300 is "optional" because it is required only for certain embodiments of the coloring system 100.

For example, when the coloring system 100 is a marking device, such as a printer, the image data source 300 is required. However, when the coloring system 100 is a system for performing a coloring operation that does not require image data, the image data source 300 is not required. An example of a coloring operation that may not require image data is an operation of making a colored food product such as cereal or the like.

The image data source 300 can be a digital camera, a scanner, or a locally or remotely located computer, or any other known or later developed device that is capable of generating electronic image data. Similarly, the image data source 300 can be any suitable device that stores and/or transmits electronic image data, such as a client or a server of a network. The image data source 300 can be integrated with the coloring system 100, as in a digital copier having an integrated scanner. Alternatively, the image data source 300 can be connected to the coloring system 100 over a connection device, such as a modem, a local area network, a wide area network, an intranet, the Internet, any other distributed processing network, or any other known or later developed connection device.

It should also be appreciated that, while the electronic image data can be generated at the time of printing an image from an original physical document, the electronic image data could have been generated at any time in the past. Moreover, the electronic image data need not have been generated from the original physical document, but could have been created from scratch electronically. The image data source 300 is thus any known or later developed device which is capable of supplying electronic image data over the link 310 to the coloring system 100. The link 310 can thus be any known or later developed system or device for transmitting the electronic image data from the image data source 300 to the coloring system 100.

Further, it should be appreciated that the links 210 and 310 can be a wired, wireless or optical link to a network (not shown). The network can be a local area network, a wide area network, an intranet, the Internet, or any other distributed processing and storage network.

The coloring system 100 includes a coloring device 120, a sensor array 130, a color revision device 140, a memory 150, a controller 160 and a spectral curve determination system 170, which are interconnected by a data/control bus 190. The spectral curve determination system 170 includes a reference database 172 and a spectral curve output device 174.

The coloring device 120 may be, for example, a print engine/printing head or marking engine/marking head, when the coloring system 100 is a printer or other marking device. The coloring device 120 may be, for example, a colorant dispenser that dispenses a colorant onto an object or into a mixture. U.S. Pat. No. 6,603,551, incorporated herein by reference in its entirety, discusses various applications for color measurement and/or adjustment, including textiles and/or textile manufacturing, and the coloring system 100 may, for example, be applied in any of these applications. Thus, the coloring device 120 may be any known or later developed device that directly or indirectly controls the final appearance of an object, material or substance.

The sensor array 130 includes multiple illuminants, such as LEDs, lasers or the like, arranged around a central photodetector (not shown), or arranged in correspondence to a plurality of photodetectors or photosites as described in, for example, U.S. Pat. No. 6,556,300, U.S. Pat. No. 6,567,170, U.S. Pat. No. 6,633,382 and/or U.S. Pat. No. 6,621,576. The illuminants will be referred to hereafter as LEDs for convenience. The number of LEDs may be any number greater than three, when a single photosensor is used, or may be as low as two when multiple photosites or photosensors are used. A larger number of LEDs gives greater accuracy, but it costs more to include more LEDs, and thus there are practical limits to the number of LEDs included in the sensor array 130, especially since an object of the systems and methods disclosed herein is to provide a low-cost spectrophotometer. Therefore, the number of LEDs is preferably from about 8 to about 16.

Each LED is selected to have a narrow band response curve in the visible range of the spectral space. Therefore, for example, ten LEDs would correspond to ten measurements in the reflectance curve. The LEDs, or other multiple illuminant based color sensor equivalent, e.g., lasers, are switched on one at a time as, for example, the measured media is passed through a transport of a printer. The reflected light is then detected by the photodetector and the corresponding voltage integrated and normalized with a white tile. The normalization is preferably performed during each measurement. For the normalization, use of a white tile calibration look-up table, which is stored in memory 150, is a standard practice in the color measurement industry. When the white tile calibration look-up table is used, the detector output is normalized to between 0 to 1 in accordance with, for example, the following equation:

$$V_{m_i} = (V_i - V_i^o) R_i^w / (V_i^{fs} - V_i^o), \quad (1)$$

where $V_i^o$ is the black measurement sensing system offset of the $i^{th}$ LED, $V_i^{fs}$ is the white tile measurement, $V_i$ is the sensor detector output, and $R_i^w$ is the reflectance spectral value of the white tile at the mean wavelength of the $i^{th}$ LED, or at a wavelength at which LED intensities are at their peak values. Any other known or later developed method for normalization may alternatively be used. $V_{m_i}$ may be compensated for temperature variation.

The color revision device 140 calibrates the output of the coloring device 120 in accordance with information obtained from the spectral curve output device 174 of the spectral curve determination system 170. This calibration may be performed as often as necessary or desired to maintain a desirable output of the coloring device 120.

The memory 150 may serve as a buffer for information coming into or going out of the coloring system 100, may store any necessary programs and/or data for implementing the functions of the coloring system 100, and/or may store data at various stages of processing. The above-mentioned white tile lookup table may be stored in the memory 150 if desired. The reference database 172, described in more detail below, may also be stored in the memory 150 if desired. Furthermore, it should be appreciated that the memory 150, while depicted as a single entity, may actually be distributed. Alterable portions of the memory 150 are, in various exemplary embodiments, implemented using static or dynamic RAM. However, the memory 150 can also be implemented using a floppy disk and disk drive, a writeable optical disk and disk drive, a hard drive, flash memory or the like. The generally static portions of the memory 150 are, in various exemplary embodiments, implemented using ROM. However, the static portions can also be implemented using other non-volatile memory, such as PROM, EPROM, EEPROM, an optical ROM disk, such as a CD-ROM or DVD-ROM, and disk drive, flash memory or other alterable memory, as indicated above, or the like.

The controller 150 controls the operation of other components of the coloring system 100, performs any necessary calculations and executes any necessary programs for implementing the processes of the coloring system 100 and its individual components, and controls the flow of data between other components of the coloring system 100 as needed.

The spectral curve determination system 170 determines and outputs spectral curves. Specifically, the spectral curve output device 174 outputs spectral curves based on a plurality of spectra which are determined by the controller 150 based on information from the reference database 172, described in more detail below, and the output of the sensor array 130 from different color targets.

To obtain an output similar to that of a reference spectrophotometer, such as a Gretag spectrophotometer, it is necessary to convert the readings from the sensory array 130 to reflectance spectra. A Gretag spectrophotometer outputs 36 spectral reflectance values, evenly spaced at 10 nm over the visible spectrum (e.g., 380 nm to 730 nm). Therefore, in the following examples, the readings from the sensor array 130 are converted to 36 reflectance values. In other words, when there are 8 LEDs in the sensor array 130, the LEDs are sequentially actuated, readings (typically voltage readings) are collected from the photodetector for each respective LED actuation, and the 8 readings (voltages) from the sensor array 130 are converted to 36 reflectance values per color. If a multiple photosite sensor is used, it will be appreciated that a desired number of outputs, for example 8 outputs, will be obtained from smaller number of LEDs, for example 3 or 4 LEDs. An X-Rite spectrophotometer has 31 outputs evenly spaced at 10 nm over the spectrum of 400 nm to 700 nm, so in the case of an X-Rite spectrophotometer the readings from the sensor array 130 are converted to 31 reflectance values.

It will be understood that each of the circuits shown in FIG. 1 can be implemented as portions of a suitably programmed general purpose computer. Alternatively, each of the circuits shown in FIG. 1 can be implemented as physically distinct hardware circuits within an ASIC, or using a FPGA, a PDL, a PLA or a PAL, or using discrete logic elements or discrete circuit elements. The particular form each of the circuits shown in FIG. 1 will take is a design choice and will be obvious and predictable to those skilled in the art.

The reference database 172 is generated by measuring the reflectance spectra of some set of reference colors, with an accurate reference spectrophotometer, such as a Gretag spectrophotometer, and their corresponding LED sensor outputs, with the sensor array 130. In general, the more densely populated the database is, i.e., the more reference colors used, the better the resulting accuracy. In one exemplary reference database, about 5,000 colors are used. Furthermore, even spacing of the reference colors in the color space gives greater accuracy. The data stored in the reference database 172 will be referred to hereafter as the training samples.

First, the sensor transfer function, i.e., the information included in the reference database 172, is a mapping from reflectance spectra (as measured by a reference spectrophotometer) to sensor outputs (as measured by the sensor array 130) formed by a set of N spectra to voltage measurements, denoted as $$\Omega = [S_1 S_2 \ldots S_N] \in R^{n \times N} \to Z = [Z_1 Z_2 \ldots Z_N] \in R^{l \times N} \quad (2)$$

where $S_1 S_2 \ldots S_N$ are the vector elements containing the N spectral curves, each curve containing 36 elements, i.e., reflectance values (n=36). Here, each curve contains 36 elements because a Gretag spectrophotometer, which outputs 36 values, is used. If a different spectrophotometer is used which has a different number of outputs, n will be a correspondingly different number. $Z_1 Z_2 \ldots Z_N$ are each a vector including 8 normalized voltages corresponding to the 8 LED color sensor outputs for a given color. R indicates the set of real numbers. N is a predetermined number based on certain color gamut specifications for the color sensor array 130. Generally, the larger the gamut, the larger will be N. As an example, N may be about 5000.

The value of l discussed above depends on the number of sensor outputs, which may be the number of illuminants, e.g., the number of LEDs. However, it will be appreciated that when a multiple photosite sensor is used, l will not be equal to the number of LEDs.

Given the vector $V_m$, which represents the set of 8 LED sensor voltages, as in Equation (1), corresponding to an unknown (target) color with true spectrum S, the goal of the algorithm is to obtain an estimate of the unknown, true spectrum S. The relationship between color spectrum and LED sensor outputs for a given color may be assumed to be linear affine, quadratic affine or cubic affine etc. Therefore, the general expression for S may be defined as $$S = AV \quad (3)$$

where $V = [V_m\ 1]$ is an 9×1 vector for a linear affine model with 8 LEDs in the sensor array 130. V is a vector formed by augmenting the normalized $V_m$ voltage vector with scalar value 1 to include an affine term. Thus, for example, if 12 LEDs were used in the sensor array 130, V would be a 13×1 vector for a linear affine model. A is an unknown conversion matrix (also called spectral reconstruction matrix or model matrix) of size 36×9 for an 8 LED sensor and a linear affine model. Those skilled in the art will appreciate that, if quadratic or other terms are included, then the number of elements in vector V and matrix A correspondingly increase to greater than 9×1 and 36×9 respectively.

To compute matrix A optimally for obtaining an estimated spectrum Ŝ for a color measured by sensor array 130, whose output is the augmented vector $V = [V_m 1]$, a weighted least square criteria is used. The optimal solution for matrix A, called $A^*$, is obtained by minimizing the objective function defined as $$A^* = \underset{A}{\operatorname{argmin}} J = \underset{A}{\operatorname{argmin}} \sum_{i=1}^{N} w(i) \|S_i - AZ_i\|^2 \quad (4)$$

where $$w(i) = \frac{1}{d(i)^p + \varepsilon}; d(i) = \|V - Z_i\| \quad (5)$$

p is an integer number greater than or equal to 2, and $\varepsilon$ is a small positive constant. i represents the index for training samples from the reference database $(S_i, Z_i)$. Appropriate values for p and $\varepsilon$ may be empirically determined. Examples of appropriate values chosen for an 8- or 10-LED sensor are p=4 and $\varepsilon = 1 \times 10^{-5}$. The solution to the above optimization problem can be easily obtained by setting the gradient of J with respect to A equal to zero. This results in, for each color, $$A^* = QP^{-1} \quad (6)$$

where $$Q = \sum_{i=1}^{N} w(i) S_i Z_i^T \quad (7)$$

and $$P = \sum_{i=1}^{N} w(i) Z_i Z_i^T \quad (8)$$

where i is an index of colors, and N is the number of colors in the training set.

Once $A^*$ is computed, the estimated spectrum Ŝ for the target color measured by the sensor array 130 can be obtained by $$\hat{S} = A^* V \quad (9)$$

The foregoing algorithm determines one spectrum, obtained from one target color under measurement. If spectral curves are to be generated for a plurality of target colors, then matrix $A^*$ is computed for the plurality of target colors, using Equations (6)-(9) for each color with corresponding V vector. The matrix $A^*$ may be further adjusted to personalize the sensor for differences in inter-sensor or environmental conditions, such as variations in mounting or mechanical tolerances, to improve accuracy. For example, a personalization process may used to construct an inter-sensor or environmental model for the sensor and to adjust a reference database. The personalization process may use as few as 75 colors for the construction Furthermore, as disclosed in co-pending U.S. patent application Ser. No. 10/758,096, the reference database may be structured in "clusters." In particular, using a cell division algorithm, such as the one described in detail below, the reference database 172 is partitioned into K cells, $\Omega_k$ for k=1, 2, 3, ... K as follows:

$$\Omega_k = [S_{1_1} S_{2_2} \ldots S_{N_k}]_k \in R^{n \times N_k} \to Z_k = [C_k V_{1_1} V_{2_2} \ldots V_{N_k}] \in R^{l \times N_k} \quad (10)$$

where $[S_{1_1} S_{2_2} \ldots S_{N_k}]_k$ are the vector elements containing the $N_k$ spectral curves for the $k^{th}$ cell. It should be appreciated that these elements are the output of the cell division algorithm. It should also be appreciated that $S_1$, $S_2$ etc. of Equation (2) described above do not necessarily correspond to $S_{1_1}$, $S_{2_2}$ of Equation (10), because of the reordering of the training sample data that occurs during the cell division process. Each of the $N_k$ spectral curves contains 36 elements, i.e., reflectance values n=36, if a spectrophotometer with 36 outputs, such as a Gretag spectrophotometer, is used for obtaining the training samples for the reference database 172. $[V_{1_1} V_{2_2} \ldots V_{N_k}]_k$ are the vector elements from the normalized LED sensor outputs, each having 8 components (l=8) when an 8-LED spectrophotometer is used for color measurement, $C_k$ is the centroid of the voltages in a kth cell, and R indicates the notation used to represent real numbers.

In the following description, K is the total number of cells into which the reference database 172 is ultimately divided, and N is a predetermined number representing the total number of color samples in the complete reference database 172. The relationship between K and N is as follows:

$$N = \sum_{k=1}^{K} N_k \quad (11)$$

where k is an index for clusters, and K is the number of clusters.

Exemplary algorithms for partitioning the reference database 172 will be described with reference to FIGS. 2-3.

Figure 2:
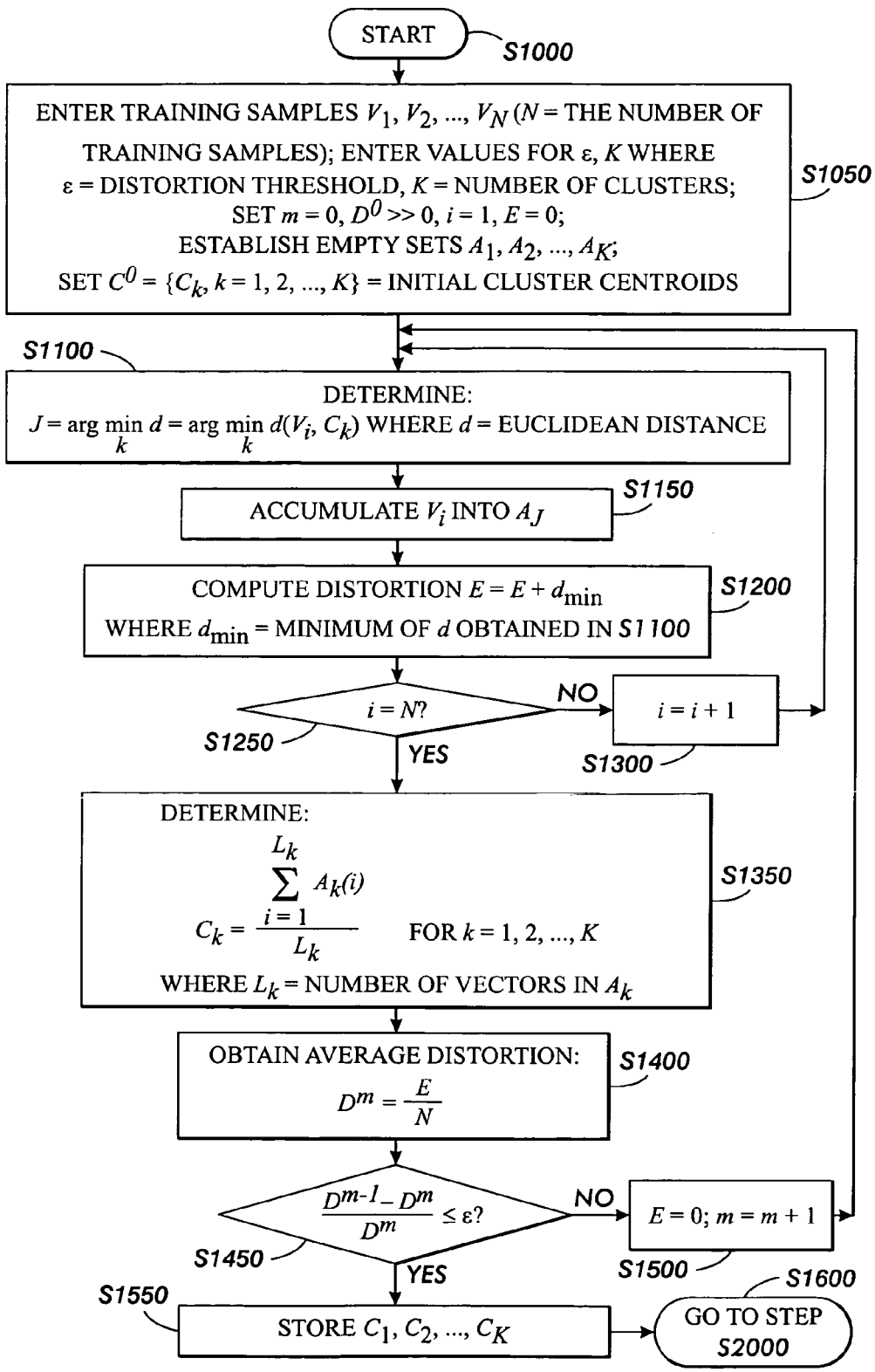
FIG. 2 is a flowchart illustrating an exemplary method of obtaining centroids for a reference database.

FIG. 2 is a flowchart illustrating a method of determining centroids. These centroids will become the centers of the respective clusters of the partitioned database. Beginning in step S1000, the process continues to step S1050, where N training samples $V_1$, $V_2$ ... , $V_N$ are entered from the reference database that is to be partitioned. Various values are entered, including $\epsilon$, K, m, $D^0$, i, and E. $\epsilon$ is a distortion threshold, which indicates the maximum allowable distortion, as defined, e.g., directly by the user, by a preset default, or based on some other criterion associated with desired system performance. K is the number of clusters into which the database is to be partitioned, and may be arbitrary or based on any desired criteria. The larger K is, the better the result obtained from the reference database, but it will be appreciated that processing time will also increase in proportion to K, and that more training samples will be required for larger K. One example of a suitable value for K is 10. m, $D^0$, i, and E are values used in the algorithm. Specifically, m and i are simply iteration counters, as will be appreciated from the flowchart, and may be initially set at 0 and 1, respectively. $D^0$ is an initial distortion setting, and is set at an arbitrary large positive number, such as 1,000. E is a distortion value, which is initially set at 0.

Additionally, empty sets $A_1$, $A_2$ ... $A_K$ are established. These are the clusters of the database, which will be filled with initial values and then updated until certain criteria are met, as described below. Initial cluster centroids $C^0$ are set equal to $C_k$, where k=1, 2, ... , K. Thus, one centroid $C_k$ is assigned to each empty set. The centroids $C_k$ may be arbitrary, or may be set using a "best guess" based on previous experience.

The process continues to step S1100 where, for each training sample $V_i$, expressed as a voltage vector, the Euclidean distance d to each cluster centroid $C_k$ is determined, and from the Euclidean distances d the cluster $A_J$ having the minimum Euclidean distance is identified as follows:

$$J = \underset{k}{\mathrm{argmin}}\, d = \underset{k}{\mathrm{argmin}}\, d(V_i, C_k) \quad (12)$$

Then, in step S1150, $V_i$ is accumulated into $A_J$. Next, in step S1200, the distortion E is determined by $$E = E + d_{min} \quad (13)$$

where $d_{min}$ is the minimum distortion value d obtained in step S1100.

Steps S1250 and S1300 perform an incrementation of i, and steps S1100 through S1200 are repeated such that the next training sample $V_i$ is considered and accumulated into the appropriate cluster $A_J$. This cycle is repeated until all training samples have been accumulated into an appropriate cluster. When i=N in step S1250, i.e., when all training samples have been accumulated, the process continues to step S1350.

In step S1350, an updated cluster centroid $C_k$ is determined for each cluster $A_1$, $A_2$, ... , $A_K$. This determination may be performed according to the following equation:

$$C_k = \frac{\sum_{i=1}^{L_k} A_k(i)}{L_k} \quad (14)$$

where $L_k$ is the number of vectors in $A_k$.

In step S1400, the average distortion $D^m$ is obtained by:

$$D^m = \frac{E}{N} \quad (15)$$

Then, in step S1450, it is determined whether distortion is within the distortion threshold $\epsilon$. This determination may be made by determining whether the following relation is satisfied:

$$\frac{D^{m-1} - D^m}{D^m} \le \varepsilon \quad (16)$$

If the relation (16) is not satisfied, the process continues to step S1500, sets E=0 and m=m+1, and repeats steps S1100 through S1450, beginning this time with the updated cluster centroids $C_k$. When the relation (16) is satisfied, the process jumps to step S1550 and stores the centroids $C_1, C_2, \ldots, C_K$.

The centroids stored in step S1550 are the "final" centroids that will be used in the partitioned reference database. After these centroids are stored, a final step of accumulating the training samples into the appropriate clusters may be performed, as described next. Continuing to step S1600, the program goes to step S2000 of FIG. 3, and initializes by inputting the cluster centroids $C_k$, where k=1, 2, ..., K, where K is the number of clusters, and by establishing empty sets $A_1, A_2, \ldots, A_K$. i is set initially at 1. The cluster centroids $C_k$ may be obtained from step S1550 of FIG. 2, but it should be appreciated that the flowchart of FIG. 3 may also be implemented with cluster centroids obtained in some other manner. For example, the centroids may be "critical colors," e.g., a subset of colors of a pantone color set, or colors used for controlling a marking device, or colors from a document obtained by processing the pixels in the document and identifying, e.g., custom colors such as colors of a company logo.

Continuing to step S2100, training samples $V_1, V_2, \ldots, V_N$ are entered. The following steps S2200 and S2300 are identical to steps S1100 and S1150, respectively, of FIG. 2, and thus each training sample $V_i$ is accumulated into the appropriate cluster, i.e., the cluster having the centroid with the shortest Euclidean distance from the training sample.

The following steps S2400 and S2500 are identical to steps S1250 and S1300, respectively, of FIG. 2, and thus an incrementation/loop is performed such that steps S2200 and S2300 are repeated and the next training sample $V_i$ is considered and accumulated into the appropriate cluster $A_j$. This cycle is repeated until all training samples have been accumulated into an appropriate cluster. When i=N in step S2400, i.e., when all training samples have been accumulated, the process continues to step S2600, stores the clusters $A_1, A_2, \ldots, A_K$ and then ends in step S2700.

Figure 3:
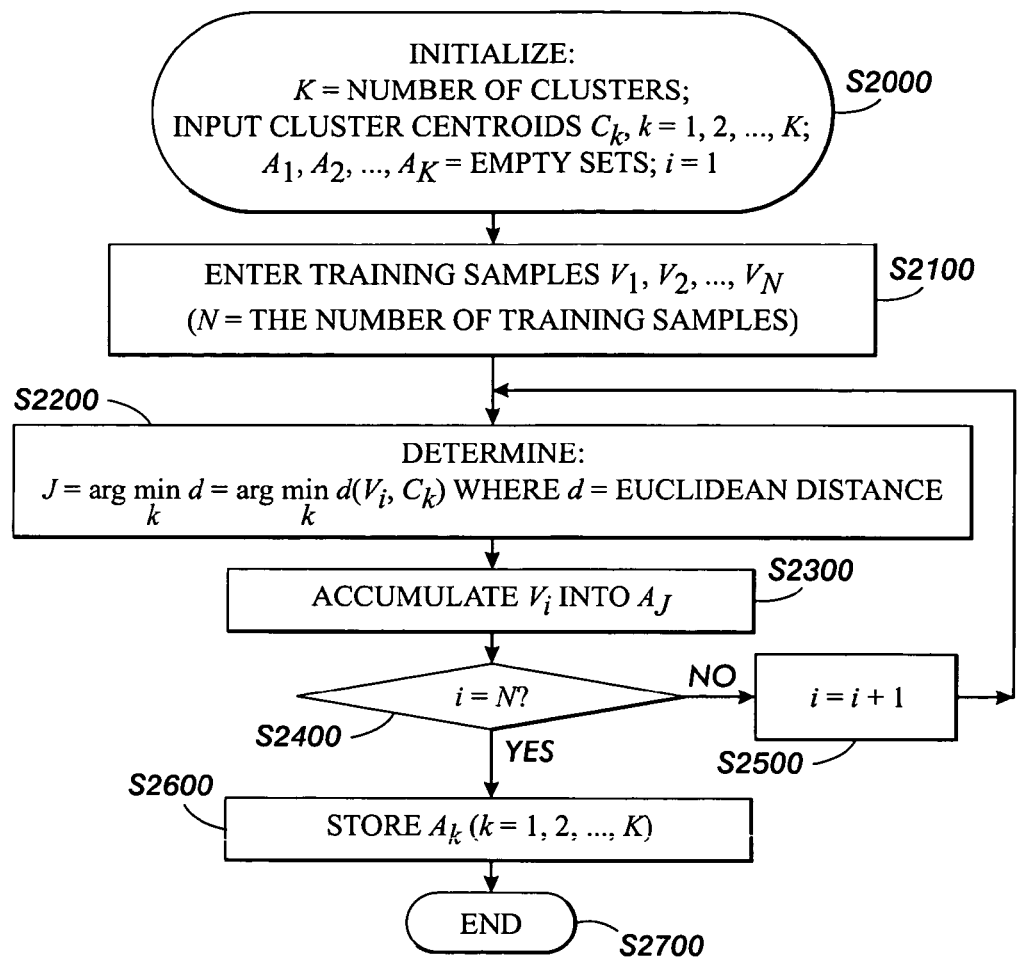
FIG. 3 is a flowchart illustrating an exemplary method of generating clusters for a reference database.

The steps from S1100 to S1500 of FIG. 2 and the steps from S2200-S2500 of FIG. 3, viewed in isolation without reference to the other steps in FIGS. 2 and 3, define a process known as vector quantization, and also known as a "K-Means algorithm" or "Lind-Buzo-Gray (LBG) algorithm."

Figure 4:
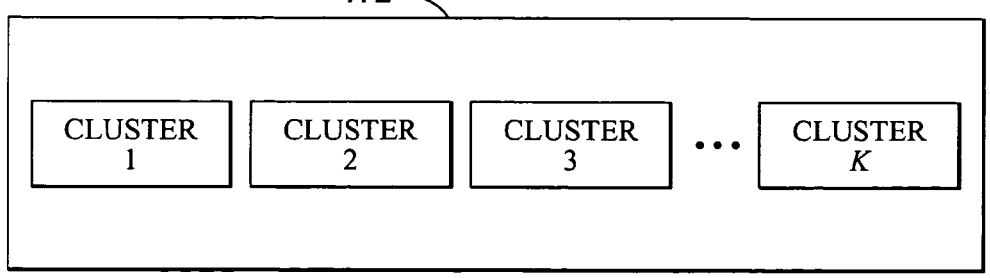
FIG. 4 illustrates an exemplary reference database.

FIG. 4 illustrates an exemplary reference database. In FIG. 4, "Cluster 1", "Cluster 2", . . . "Cluster K" correspond respectively to "$A_1$", "$A_2$", . . . "$A_K$" of FIG. 3. Thus, the reference database is structured with clusters.

The foregoing algorithm is applied at nominal temperature, i.e., the temperature at the time the sensor was characterized, to determine "$A_1$", "$A_2$", . . . "$A_K$." If spectral curves are to be generated for each target color for a plurality of temperature ranges, then "$A_1$", "$A_2$", . . . "$A_K$" may be functions of temperature and may be stored for a range of temperatures.

It will be appreciated that $A_k$ (k=1, 2, . . . K) at this point corresponds to $Z_k$, without the centroid $C_k$, of Equation (10) described above. Thus, the values for $A_k$ represent only the voltages from the cell divisional algorithm described above. It will be appreciated that if the spectral reconstruction algorithm that will be implemented using the partitioned database requires the full training sample data, rather than just the voltages, then the training sample data corresponding to the voltages represented by $A_k$ will need to be entered as well. For example, the Dynamic Least Squares (DLS) algorithm described in U.S. Pat. No. 6,721,692 requires the full training sample data. In this instance, the training sample data corresponds to $\Omega_k$ of Equation (10) described above. Thus, the data generated for a kth cluster would correspond to $B_k = \{\Omega_k, Z_k\}$, which incorporates both spectral and voltage functions pertaining to training samples in the Kth cluster. It should be appreciated that the specific algorithm used may also require that the centroids $C_k$ be included. Thus, step S2600 of FIG. 3 may include storing $B_k$ and/or the centroids $C_k$ in addition to or instead of storing $A_k$.

Exemplary algorithms that may be implemented by the controller 160 for determining spectra based on the reference database 172 and the output of the sensor array 130 are described in U.S. Pat. No. 6,721,692, U.S. Pat. No. 6,584,435 and U.S. Pat. No. 6,587,793, each of which is incorporated herein by reference in its entirety. An algorithm is described below in which interaction with the reference database is more specifically described. It should be appreciated that any of the above-mentioned algorithms may be implemented within the algorithm described below, or that the algorithm described below may be implemented independently of any of the above-mentioned algorithms. Those skilled in the art will understand how, for example, to implement the algorithm described below in conjunction with any of the above-mentioned algorithms. It has been found that it is particularly effective, from the standpoint of processing speed and accuracy, when the algorithm described below is implemented in connection with the algorithm disclosed in U.S. Pat. No. 6,721,692.

The partitioned database may be used directly using, e.g., the spectral reconstruction algorithm disclosed in the above-mentioned U.S. Pat. No. 6,721,692. Alternatively, for reasons of efficiency and cost, the partitioned reference database may be used indirectly by constructing a linear or non-linear model using the centroids $C_k$ and/or data in $B_k$, described above, and then using the model as the database in a spectral reconstruction algorithm.

With a structured reference database having models for different temperatures and clusters ($A_k$, $C_k$ or $B_k$), compensation may be provided for temperature induced peak wavelength shift of LEDs (or other illuminants) in spectrophotometers. Different clusters may contain different numbers of colors. The spectral reconstruction matrices $A^*_k(T_1)$ may be constructed using equation (6) for cluster k, k=1, 2, . . . K, in which K corresponds to the number clusters. In the following description, $A^*_k(T_1)$ will represent a spectral reconstruction matrix obtained from corresponding clusters $A_1, A_2, \ldots, A_k$, k=1, 2, . . . K, for temperature $T_1$. Similarly, $A^*_k(T_i)$, i=0, 1, 2 . . . g, where g is an integer representing the number of temperatures, represent a plurality of such spectral reconstruction matrices for different temperatures $T_i$, i=0, 1, 2 . . . g, respectively, for cluster k, k=1, 2, . . . K. The desired number of temperatures (g) may depend on specific applications. The larger the number g, the more accurate a measurement may become, but the more processing resources, e.g., processing time are consumed. As discussed below in connection with FIG. 5, an exemplary system measures the operating temperature and interpolates between models for different temperatures to estimate the appropriate model to use at the temperature of interest. The estimated model is then used to perform the spectral reconstruction. This may be done in real-time. If the temperature corresponds exactly to one of the temperatures $T_i$, the interpolation will not be performed, and that temperature will be used as-is.

Figure 5:
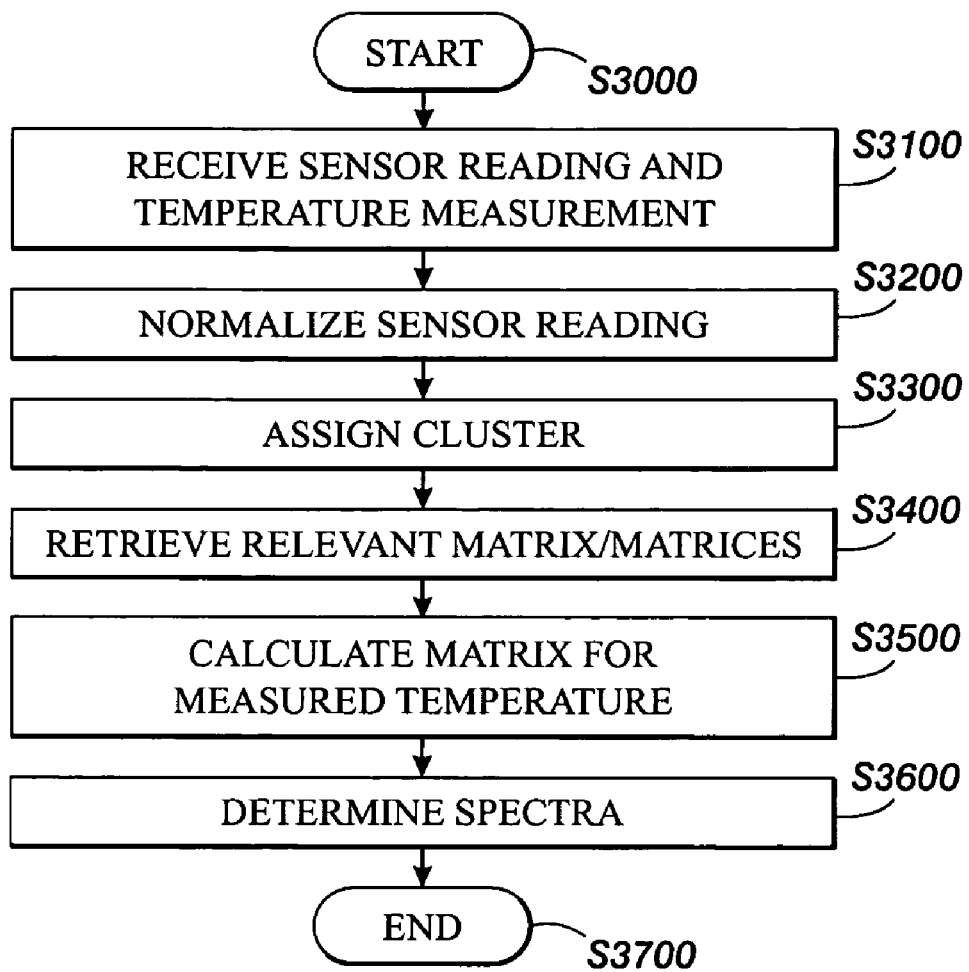
FIG. 5 is a flowchart illustrating an exemplary method of determining spectra.

FIG. 5 is a flowchart illustrating an exemplary method of determining a spectrum, using stored matrices for different temperatures and different clusters, obtained as described above. Beginning in step S3000, the process continues to step S3100, where sensor readings are received from illuminants in a sensor array. Also received is a temperature measurement indicating an operating temperature under which the sensor readings are obtained. Continuing to step S3200, the sensor readings are normalized. The process then continues to step S3300.

In step S3300, a cluster is determined by using a centroid and sensor reading. For example, a Euclidean distance from the sensor reading to each stored cluster centroid may be determined, and it is determined which of these Euclidean distances is the shortest. The cluster corresponding to the shortest Euclidean distance is determined to be the cluster for the sensor reading.

It should be appreciated that using clusters is optional. Thus, while various embodiments incorporate cluster assignment, various other embodiments do not incorporate cluster assignment. Accordingly, in various other embodiments, step S3300 may be skipped.

Continuing to step S3400, model information is retrieved from the storage for the determined cluster and based on the temperature measurement. In particular, relevant model matrix or model matrices is/are retrieved from the storage for the determined cluster based on the temperature measurement. For example, two matrices for the determined cluster may be retrieved, with the two temperatures corresponding to the two matrices being close to and bracketing the temperature measurement. Then, in step S3500, the matrix for the temperature measurement is calculated by interpolating the two retrieved matrices. For example, for a temperature measurement T, two matrices $A^*_k(T_i)$ and $A^*_k(T_{i+1})$ may be retrieved, with:

$$T_i \leq T \leq T_{i+1}, \quad (17)$$

The matrix for T may be obtained by:

$$A^*_k(T) = \left(1 - \frac{T - T_i}{T_{i+1} - T_i}\right)A^*_k(T_i) + \left(\frac{T - T_i}{T_{i+1} - T_i}\right)A^*_k(T_{i+1}). \quad (18)$$

Alternatively, when there are models for only two temperatures stored in the database, a single matrix $A^*_k(T_0)$ with its corresponding temperature $T_0$ closest to the temperature measurement T may be retrieved in step S3400. The matrix for T may be calculated in step S3500 as an extrapolation of the single matrix $A^*_k(T_0)$:

$$A^*_k(T) = A^*_k(T_0) + \left(\frac{T - T_0}{T_1 - T_0}\right)(A^*_k(T_1) - A^*_k(T_0)) \quad (19)$$

$$= A^*_k(T_0) + \left(\frac{\partial A^*_k}{\partial T}\right)(T - T_0)$$

where $$\left(\frac{\partial A^*_k}{\partial T}\right) \triangleq \frac{1}{T_1 - T_0}(A^*_k(T_1) - A^*_k(T_0)) \quad (20)$$

may be a pre-calculated value based on a known parameter $A^*_k(T_1)$.

As discussed above, if the temperature corresponds exactly to one of the temperatures $T_i$, the interpolation will not be performed. Under such circumstances, step S3500 may be omitted.

Next, in step S3600, the spectrum for the sensor reading is determined based on the calculated matrix according to Equation (21) below:

$$\hat{S} = A^*_k V \quad (21)$$

which is similar to Equation (9). Finally, the process ends in step S3700.

The spectrophotometer described above belongs to a class of color parameter measuring devices that use a model or lookup table to associate raw sensor measurements with their respective color parameter values. The model or lookup table may be based on a "training" data set derived from measurements on a reference color parameter measuring device, wherein the reference color parameter measuring device is of greater accuracy with respect to the true color parameter values. Other LED based color parameter measuring devices also fall into this class. For example, the colorimeter described above also may be in this class. A densitometer that is calibrated to produce CIELAB L* values may be another example of this class of color parameter measuring device. "Color Parameters" in this context is meant to describe Reflectance Spectrum, CIELAB [L* a* b*] values, and other color description quantities. Since these devices use LED illumination, they are also subject to temperature induced spectral content variations, and will exhibit loss of accuracy when operated in environments of varying temperature. The method described here may also be applied in these cases, as follows. The following equation describes an exemplary color parameter measuring device that uses a model or lookup table to convert raw measurements to color parameter estimates:

$$\hat{E} = f(\underline{V}; \{E_n\}, \{\underline{V}_n\}) \quad (22)$$

where f is a matrix and:
  $\hat{E}$=Vector of Color Parameters
  $\underline{V}$=Vector of Sensor Measurements
  $\{E_n\}$=Set of Color Parameter Values used in Device Characterization
  $\{\underline{V}_n\}$=Set of Sensor Measurements used in Device Characterization
  n=1,2, . . . , N
  N=Number of Data Pairs used in Device Characterization.

Data used in the device characterization include or are used to derive the model and/or the lookup tables, as indicated in, for example, Equation (21). Now, with temperature variations, this equation becomes a function of temperature, as well:

$$\hat{E}(T_i) = f(\underline{V}; \{E_n\}, \{\underline{V}_n\}, T_i) \quad (23)$$

The method described here may be applied to any device in this class, using the following equation, which is a general case of Equations (18) and (21):

$$\hat{E}(T) = \left(1 - \frac{T - T_i}{T_{i+1} - T_i}\right)f(\underline{V}; \{E_n\}, \{\underline{V}_n\}, T_i) + \left(\frac{T - T_i}{T_{i+1} - T_i}\right)f(\underline{V}; \{E_n\}, \{\underline{V}_n\}, T_{i+1}) \quad T_i \leq T \leq T_{i+1} \quad (24)$$

Thus this method may be applied to any color parameter measuring system that uses LED illumination and a model or lookup table to determine its color parameter value estimates.

While linear interpolation has been described here, the method may use any interpolation scheme to estimate the color parameter values, including polynominal interpolation, spline interpolation, and interpolation using various basis functions.

The method illustrated in FIG. 5 may be implemented in a computer program product that can be executed on a computer. The computer program product may be a computer-readable recording medium on which a control program is recorded, or it may be a transmittable carrier wave in which the control program is embodied as a data signal.

Figure 6:
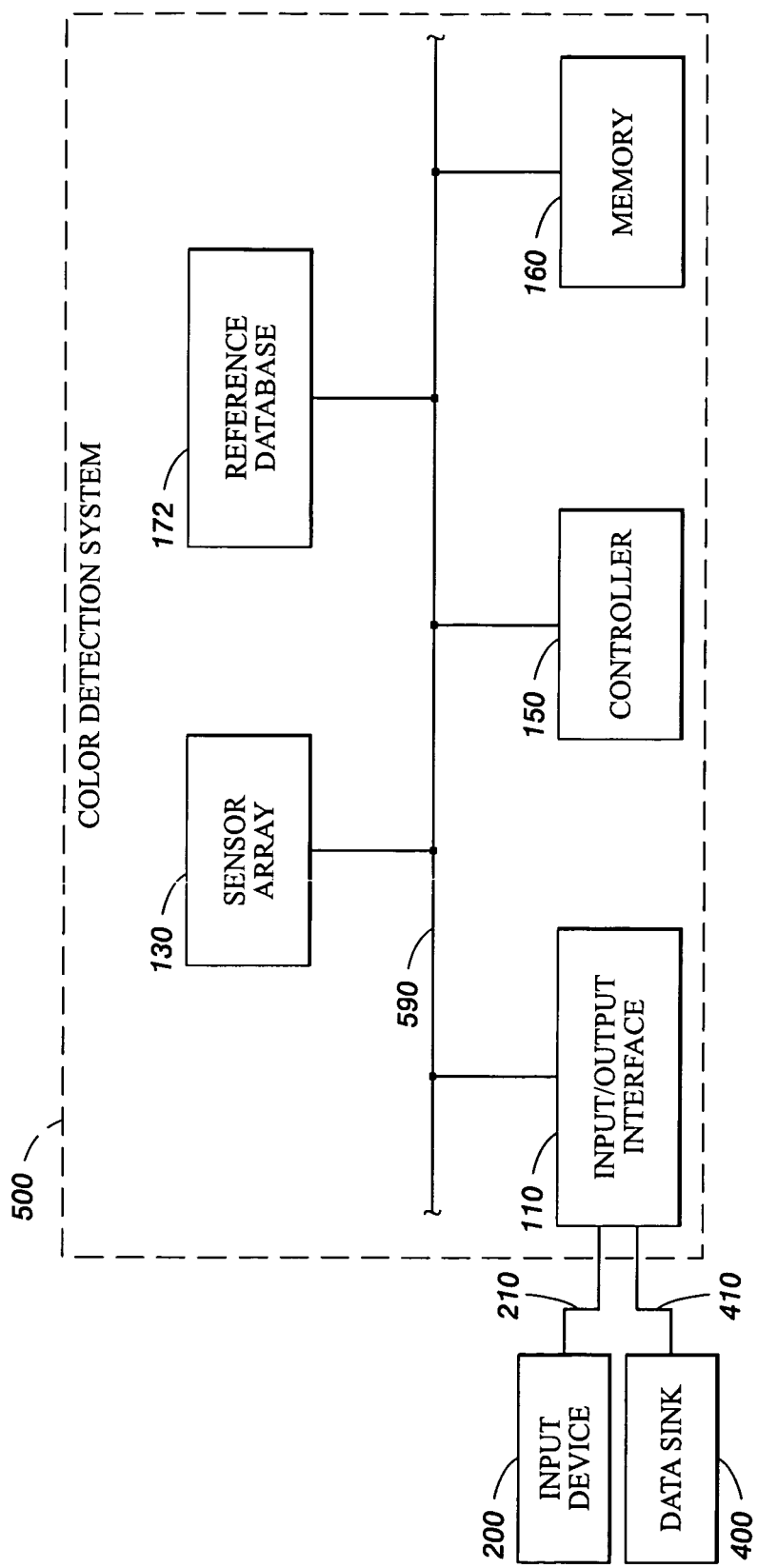
FIG. 6 is a functional block diagram illustrating an exemplary embodiment of a color detection system.

FIG. 6 is a functional block diagram illustrating an exemplary embodiment of a color detection system 500. The color detection system 500 includes an input/output interface 110, a sensor array 130, a controller 150, a memory 160 and a reference database 172, which may be identical to the corresponding elements of FIG. 1, interconnected by a data/control bus 590. The color detection system 500 is connected to a user input device 200 via a link 210, similar to the input device 200 and link 210 described above in conjunction with FIG. 1. The color detection system 500 is also connected to a data sink 400 via a link 410 which, like the links 210 and 310, can be a wired, wireless or optical link to a network (not shown). In general, the data sink 400 can be any device that is capable of outputting or storing the processed data generated by the color detection system, such as a printer, a copier or other image forming devices, a facsimile device, a display device, a memory, or the like.

The color detection system 500 may be, or be included in, a portable or stationary unit designed specifically to measure color of a target object. In use, the color detection system 500 is positioned with the sensor array 130 facing the target object, the sensor array 130 is activated as described above, and then the above-described algorithm is executed by the controller 150, using data from the sensor array 130 and the reference database 172, to obtain an estimated spectrum of the target object. The estimated spectrum is then output to the data sink 400.

From the foregoing descriptions, it can be appreciated that, in embodiments, a calibration tool for scanners, printers, digital photocopiers, etc. may be provided, and that, in embodiments, a color measurement tool may be designed to provide one-time color measurements of target objects.

The coloring system 100 of FIG. 1 and the color detection system 500 of FIG. 6 are preferably implemented either on a single program general purpose computer or separate programmed general purpose computers, with an associated sensor array 130 (and coloring device 120, in the case of FIG. 1). However, the coloring system 100 and color detection system 500 can also be implemented on a special purpose computer, a programmed micro-processor or microcontroller and peripheral integrated circuit element, an ASIC or other integrated circuit, a digital signal processor, a hard-wired electronic or logic circuit such as a discrete element circuit, a programmable logic device such as a PLD, PLA, FPGA, PAL, or the like. In general, any device capable of implementing a finite state machine that is in turn capable of implementing the flowcharts shown in FIG. 5, or appropriate portions thereof, can be used to implement the spectral curve reconstruction device.

Furthermore, the disclosed methods may be readily implemented in software using object or object-oriented software development environments that provide portable source code that can be used on a variety of computer or workstation hardware platforms. Alternatively, appropriate portions of the disclosed coloring system 100 and the color detection system 500 may be implemented partially or fully in hardware using standard logic circuits or a VLSI design. Whether software or hardware is used to implement the systems is dependent on the speed and/or efficiency requirements of the system, the particular function, and the particular software or hardware systems or microprocessor or microcomputer systems being utilized. The processing systems and methods described above, however, can be readily implemented in hardware or software using any known or later developed systems or structures, devices and/or software by those skilled in the applicable art without undue experimentation from the functional description provided herein together with a general knowledge of the computer arts.

Moreover, the disclosed methods may be readily implemented as software executed on a programmed general purpose computer, a special purpose computer, a microprocessor, or the like. In this case, the methods and systems disclosed herein can be implemented as a routine embedded on a personal computer or as a resource residing on a server or workstation, such as a routine embedded in a photocopier, a color photocopier, a printer driver, a scanner, or the like. The systems and methods can also be implemented by physical incorporation into a software and/or hardware system, such as the hardware and software system of a photocopier or a dedicated image processing system.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art which are also intended to be encompassed by the following claims.

What is claimed is:

1. A method of determining color parameter values, comprising:

obtaining a plurality of illuminant sensor outputs, each illuminant sensor output obtained by illuminating a target at an operating temperature;

obtaining a measurement of the operating temperature;

retrieving model information from a reference database based on the operating temperature and the sensor outputs, the reference database containing different model information for different temperatures;

determining a model for the operating temperature and the sensor outputs based on the retrieved model information;

determining color parameter values based on the determined model; and outputting the determined color parameter values to an output media.

2. The method of claim 1, wherein the color parameter values are reflectance spectra.

3. The method of claim 1, wherein the color parameter values are L*,a*,b* values.

4. The method of claim 1, wherein the color parameter values are R,G,B, values.

5. The method of claim 1, wherein the color parameter values are X,Y,Z, values.

6. The method of claim 1, further comprising establishing the reference database, the establishing the reference database comprising:

establishing a plurality of temperatures, and for each temperature:
  constructing a spectral reconstruction matrix including a plurality of training samples, each training sample correlating a reference spectrum with a corresponding plurality of normalized illuminant sensor outputs for reference colors of the temperature; and
  storing the spectral reconstruction matrices in the reference database.

7. The method of claim 1, wherein
the model information includes matrices for converting illuminant sensor outputs to color parameters, each matrix being trained for a respective temperature,
the retrieved model information includes two matrices corresponding to two temperatures that bracket the operating temperature,
determining the model comprises determining a color parameter vector as:

$$\hat{E}(T) =$$
$$\left(1 - \frac{T - T_i}{T_{i+1} - T_i}\right) f(\underline{V}; \{\underline{E}_n\}, \{\underline{V}_n\}, T_i) + \left(\frac{T - T_i}{T_{i+1} - T_i}\right) f(\underline{V}; \{\underline{E}_n\}, \{\underline{V}_n\}, T_{i+1})$$
$$T_i \le T \le T_{i+1}$$

where T is the operating temperature, $T_i$ and $T_{i+1}$ are the two temperatures that bracket the operating temperature, $f(\underline{V};\{\underline{E}_n\},\{\underline{V}_n\},T_i)$ and $f(\underline{V};\{\underline{E}_n\},\{\underline{V}_n\},T_{i+1})$ are the retrieved two matrices for temperatures $T_i$ and $T_{i+1}$, respectively, and:
$\hat{E}$=Vector of Color Parameters
$\underline{V}$=Vector of Sensor Measurements
$\{\underline{E}_n\}$=Set of Color Parameter Values used in Device Characterization
$\{\underline{V}_n\}$=Set of Sensor Measurements used in Device Characterization
n =1,2, . . . , N
N=Number of Data Pairs used in Device Characterization.

8. The method of claim 1, wherein the model information includes matrices for converting illuminant sensor outputs to spectra, each matrix being trained for a respective temperature.

9. The method of claim 8, wherein
the retrieved model information includes two matrices corresponding to two temperatures that bracket the operating temperature, and
determining the model comprises interpolating the retrieved two matrices to obtain a matrix for the operating temperature.

10. The method of claim 9, wherein the matrix for the operating temperature is calculated as:

$$A*(T) = \left(1 - \frac{T - T_i}{T_{i+1} - T_i}\right) A*(T_i) + \left(\frac{T - T_i}{T_{i+1} - T_i}\right) A*(T_{i+1}),$$

where T is the operating temperature, $A*(T_i)$ and $A*(T_{i+1})$ are the retrieved two matrices for temperatures $T_i$ and $T_{i+1}$, respectively, and:

$$T_i \le T \le T_{i+1}.$$

11. The method of claim 8, wherein
the retrieved model information includes a matrix corresponding to a temperature that is closest to the operating temperature, and determining the model comprises calculating a matrix for the operating temperature using an extrapolation of the retrieved matrix.

12. The method of claim 11, wherein the matrix for the operating temperature is calculated as:

$$A*(T) = A*(T_0) + \left(\frac{T - T_0}{T_1 - T_0}\right)(A*(T_1) - A*(T_0))$$
$$= A*(T_0) + \left(\frac{\partial A*}{\partial T}\right)(T - T_0)$$

where T is the operating temperature, $A*(T_0)$ is the retrieved matrix for temperature grids $T_0$, and $$\left(\frac{\partial A*}{\partial T}\right) \triangleq \frac{1}{T_1 - T_0}(A*(T_1) - A*(T_0))$$

is a pre-calculated value determined based on a known parameter $A*(T_1)$.

13. The method of claim 1, the reference database containing clusters, each cluster containing a plurality of colors, the method further comprising:
determining an appropriate cluster based on the normalized value,
wherein:
  retrieving the model information comprises retrieving model information based on the determined cluster and the operating temperature; and
  determining the model comprises determining a model for the determined cluster and the operating temperature.

14. The method of claim 13, wherein determining the cluster comprises determining a Euclidean distance.

15. A computer-readable medium having computer-executable instructions for performing the method recited in claim 1.

16. A color parameter value determination system, comprising:
a plurality of illuminants;
at least one photodetector that detects light originating from the plurality of illuminants and reflected by a target; and
a controller that:
  processes the plurality of illuminant sensor outputs obtained from at least one photodetector at an operating temperature, each illuminant sensor output indicating a color value obtained from a target;
  obtains a measurement of the operating temperature;
  retrieves model information from the reference database based on the operating temperature and the sensor outputs, the reference database containing different model information for different temperatures;
  determines a model for the operating temperature and the sensor outputs based on the retrieved model information;
  determines a color parameter value based on the determined model; and
  outputs the determined color parameter value to an output media.

17. The system according to claim 16, wherein the color parameter values are reflectance spectra.

18. The system according to claim 16, wherein the color parameter values are L*,a*,b* values.

19. The system according to claim 16, wherein the color parameter values are R,G,B, values.

20. The system according to claim 16, wherein the color parameter values are X,Y,Z, values.

21. The system according to claim 16, further comprising:
a memory that pre-stores the reference database,
wherein the controller establishes a plurality of temperatures, and, for each temperature:
constructs a spectral reconstruction matrix including a plurality of training samples, each training sample correlating a reference spectrum with a corresponding plurality of normalized illuminant sensor outputs for reference colors of the temperature; and
stores the spectral reconstruction matrices in the reference database.

22. The system according to claim 16, wherein
the model information includes matrices for converting illuminant sensor outputs to color parameters, each matrix being trained for a respective temperature,
the retrieved model information includes two matrices corresponding to two temperatures that bracket the operating temperature,
determining the model comprises determining a color parameter vector as:

$$\hat{E}(T) = \left(1 - \frac{T - T_i}{T_{i+1} - T_i}\right) f(\underline{V}; \{\underline{E}_n\}, \{\underline{V}_n\}, T_i) + \left(\frac{T - T_i}{T_{i+1} - T_i}\right) f(\underline{V}; \{\underline{E}_n\}, \{\underline{V}_n\}, T_{i+1})$$

$$T_i \leq T \leq T_{i+1}$$

where T is the operating temperature, $T_i$ and $T_{i+1}$ are the two temperatures that bracket the operating temperature, $f(\underline{V};\{\underline{E}_n\}, \{\underline{V}_n\},T_i)$ and $f(\underline{V};\{\underline{E}_n\}, \{\underline{V}_n\},T_{i+1})$ are the retrieved two matrices for temperatures $T_i$ and $T_{i+1}$, respectively, and:
$\hat{E}$=Vector of Color Parameters
$\underline{V}$=Vector of Sensor Measurements
$\{\underline{E}_n\}$=Set of Color Parameter Values used in Device Characterization
$\{\underline{V}_n\}$=Set of Sensor Measurements used in Device Characterization
n =1,2, . . . , N
N =Number of Data Pairs used in Device Characterization.

23. The system of claim 16, wherein the model information includes matrices for converting illuminant sensor outputs to spectra, each matrix being trained for a temperature.

24. The system of claim 23, wherein
the retrieved model information includes two matrices corresponding to two temperature grid points that bracket the operating temperature, and
the controller interpolates the retrieved two matrices to obtain a matrix for the operating temperature.

25. The system of claim 24, wherein the matrix for the operating temperature is calculated as:

$$A*(T) = \left(1 - \frac{T - T_i}{T_{i+1} - T_i}\right) A*(T_i) + \left(\frac{T - T_i}{T_{i+1} - T_i}\right) A*(T_{i+1}),$$

where T is the operating temperature, $A*(T_i)$ and $A*(T_{i+1})$ are the retrieved two matrices for temperature grid points $T_1$ and $T_{i+1}$, respectively, and:

$$T_i \leq T \leq T_{i+1}.$$

26. The system of claim 23, wherein
the retrieved model information includes a matrix corresponding to a temperature grid point that is closest to the operating temperature, and
the controller calculates a matrix for the operating temperature using an extrapolation of the retrieved matrix.

27. The system of claim 26, wherein the matrix for the operating temperature is calculated as:

$$A*(T) = A*(T_0) + \left(\frac{T - T_0}{T_1 - T_0}\right)(A*(T_1) - A*(T_0))$$

$$= A*(T_0) + \left(\frac{\partial A*}{\partial T}\right)(T - T_0)$$

where T is the operating temperature, $A*(T_0)$ is the retrieved matrix for temperature grid points $T_0$, and $$\left(\frac{\partial A*}{\partial T}\right) \triangleq \frac{1}{T_1 - T_0}(A*(T_1) - A*(T_0))$$

is a pre-calculated value determined based on a known parameter A*(T1) and T1.

28. The system of claim 16, the reference database containing clusters, each cluster containing a plurality of colors, wherein the controller:
determines an appropriate cluster based on the normalized value;
retrieves the model information based on the determined cluster and the operating temperature; and
determines the model for both the determined cluster and the operating temperature.

29. The system of claim 28, wherein the controller determines a Euclidean distance.

30. A coloring system incorporating the system of claim 16.

31. The coloring system of claim 30, wherein the coloring system is one of a digital photocopier and a color printer.

32. The coloring system of claim 30, wherein the coloring system is a xerographic color printer.

33. The coloring system of claim 30, wherein the coloring system is an ink-jet printer or solid ink-jet printer.

34. A color detection system incorporating the system of claim 16.

* * * * *